(12) United States Patent
Andersen et al.

(10) Patent No.: US 10,213,554 B2
(45) Date of Patent: Feb. 26, 2019

(54) ACCESSORY DEVICE WITH MOUNTING SAFETY FEATURE

(71) Applicant: Novo Nordisk A/S, Bagsværd (DK)

(72) Inventors: Jens Christian Andersen, Roskilde (DK); Preben Mikael Nielsen, Holbaek (DK); Nikolaj Eusebius Jakobsen, Soeborg (DK); Nikolaj Frogner Krusell, Risskov (DK)

(73) Assignee: Novo Nordisk A/S, Bagsværd (DK)

( * ) Notice: Subject to any disclaimer, the term of this patent is extended or adjusted under 35 U.S.C. 154(b) by 0 days.

(21) Appl. No.: 15/551,727

(22) PCT Filed: Feb. 25, 2016

(86) PCT No.: PCT/EP2016/053964
§ 371 (c)(1),
(2) Date: Aug. 17, 2017

(87) PCT Pub. No.: WO2016/135236
PCT Pub. Date: Sep. 1, 2016

(65) Prior Publication Data
US 2018/0036484 A1      Feb. 8, 2018

(30) Foreign Application Priority Data

Feb. 27, 2017  (EP) .................................... 15156963

(51) Int. Cl.
*A61M 5/00*    (2006.01)
*A61M 5/24*    (2006.01)
(Continued)

(52) U.S. Cl.
CPC ............ *A61M 5/2455* (2013.01); *A61M 5/20* (2013.01); *A61M 5/24* (2013.01);
(Continued)

(58) Field of Classification Search
CPC ............ A61M 2005/3126; A61M 5/20; A61M 5/2455; A61M 5/31553;
(Continued)

(56) References Cited

U.S. PATENT DOCUMENTS 6,482,185 B1    11/2002  Hartmann
7,195,616 B2 *   3/2007  Diller ................ A61M 5/31535
                                                                604/207

(Continued)

FOREIGN PATENT DOCUMENTS

WO         9902210 A1    1/1999
WO      2003005891 A1    1/2003
(Continued)

*Primary Examiner* — Jason Flick
(74) *Attorney, Agent, or Firm* — Wesley Nicolas

(57) ABSTRACT

A medial assembly comprises a logging first unit adapted to be mounted on a drug delivery device second unit from a fully un-mounted to a fully mounted position along a path. The first unit comprises a switch operatable between an off- and an on-state when the first unit is mounted on the second unit, the switch being in the on-state when the first unit is mounted within a first distance from the fully mounted position, and in the off-state when the first unit is mounted outside the first distance from the fully mounted position, and a snap lock operatable from an initial state through an expanded state to a snap-in state when the first unit is mounted on the second unit, the snap lock being in the snap-in state when the first unit is mounted within a second distance from the fully mounted position, the second distance being shorter than the first distance. By this arrangement it is ensured that the switch will be in the on-state before the snap lock is in the snap-in state.

11 Claims, 7 Drawing Sheets

(51) Int. Cl.
*A61M 5/20* (2006.01)
*A61M 5/315* (2006.01)
*G06F 19/00* (2018.01)
*A61M 5/31* (2006.01)

(52) U.S. Cl.
CPC ......... *A61M 5/31553* (2013.01); *G06F 19/00* (2013.01); *G06F 19/3456* (2013.01); *A61M 5/2466* (2013.01); *A61M 2005/3126* (2013.01); *A61M 2205/3317* (2013.01); *A61M 2205/502* (2013.01); *A61M 2205/60* (2013.01); *A61M 2205/6072* (2013.01)

(58) Field of Classification Search
CPC .... A61M 2205/3317; A61M 2205/502; A61M 2205/60; A61M 2205/6072; A61M 5/24; A61M 5/2466; G06F 19/3456; G06F 19/00
USPC ........................................................ 604/187
See application file for complete search history.

(56) References Cited

U.S. PATENT DOCUMENTS

| | | | |
|---|---|---|---|
| 2009/0318865 A1* | 12/2009 | Moller | A61M 5/31553 604/135 |
| 2011/0295215 A1* | 12/2011 | Nielsen | G16H 20/17 604/257 |
| 2014/0114277 A1 | 4/2014 | Eggert et al. | |

FOREIGN PATENT DOCUMENTS

| | | |
|---|---|---|
| WO | 2007107564 A1 | 9/2007 |
| WO | 2010037828 A1 | 4/2010 |
| WO | 2010052275 A2 | 5/2010 |
| WO | 2010/098928 A1 | 9/2010 |
| WO | 2013120776 A1 | 8/2013 |
| WO | 2014161952 A1 | 10/2014 |

\* cited by examiner

ACCESSORY DEVICE WITH MOUNTING SAFETY FEATURE

CROSS-REFERENCE TO RELATED APPLICATIONS

This application is a 35 U.S.C. § 371 National Stage application of International Application PCT/EP2016/053964 (published as WO 2016/135236), filed Feb. 25, 2016, which claims priority to European Patent Application 15156963.9, filed Feb. 27, 2015; the contents of which are incorporated herein by reference.

The present invention generally relates to medical devices for which the generation, collecting and storing of data are relevant. In specific embodiments the invention relates to devices and systems for capturing and organizing drug delivery dose data in a reliable and user-friendly way.

BACKGROUND OF THE INVENTION

In the disclosure of the present invention reference is mostly made to drug delivery devices comprising a threaded piston rod driven by a rotating drive member, such devices being used e.g. in the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, and the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of injection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices either durable or prefilled. The latter devices are to be discarded after being emptied and so inexpensive that it is not cost-effective to build-in electronic data acquisition functionality in the device it-self. Addressing this problem a number of solutions have been proposed which would help a user to generate, collect and distribute data indicative of the use of a given medical device.

For example, WO 2007/107564 describes an electronic "add-on" module adapted to be attached to and measure signals generated by a mechanical pen device. The detected signals may be used to detect different events, e.g. different sounds indicating setting a dose, respectively injecting a dose. A memory stores detected doses together with a time stamp, e.g. for several months. The module is provided with wireless means for transmitting detected data to an external unit, e.g. computer or another portable device (e.g. cell phone or PDA) for further processing and visualization. WO 2010/037828 discloses an arrangement for mounting such a module on a pen-formed drug delivery device. Further external devices for a pen device are shown in U.S. Pat. No. 6,482,185, and WO 03/005891. WO 2013/120776 discloses an add-on device with a mounting switch and a closure member with a snap.

As the external device is designed to detect signals or events originating from the device to which it is attached it is important that the two devices are correctly positioned relatively to each other to ensure proper operation and prevent incorrect measurements.

Having regard to the above, it is an object of the present invention to provide devices and methods allowing secure, easy and cost-effective operation of a medical assembly comprising a user-mountable module.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first general aspect of the invention an assembly comprising a first unit and a second unit is provided, wherein the first unit is adapted to be mounted on the second unit from a fully un-mounted to a fully mounted position along a path. The assembly comprises a switch and a snap lock. The switch is operatable between an off- and an on-state when the first unit is mounted on the second unit, the switch being in the on-state when the first unit is mounted within a first distance from the fully mounted position, and in the off-state when the first unit is mounted outside the first distance from the fully mounted position. The snap lock is operatable from an initial state (i.e. non-expanded) through an expanded state to a snap-in state when the first unit is mounted on the second unit, the snap lock being in the snap-in state when the first unit is mounted within a second distance from the fully mounted position, wherein the second distance is shorter than the first distance.

By this arrangement it is ensured that the switch will be in the on-state before the snap lock is in the snap-in state.

In an exemplary embodiment the second unit is a drug delivery device and the first unit is a logging module. The drug delivery device comprises a drug reservoir or means for receiving a drug reservoir, dose setting means, and drug expelling means for expelling a set dose. Alternatively the device may be a fixed dose device with the logging module logging time only. The logging module comprises electronic circuitry adapted to create a log of expelled dose amounts of drug, the electronic circuitry comprising sensor means adapted to capture a property value related to a dose amount of drug expelled from a reservoir by the expelling means during an expelling event, and processor means adapted to determine dose amounts based on captured property values.

In an exemplary embodiment the electronic circuitry with the switch in the on-state is adapted to detect an error condition corresponding to a state in which the first unit is not in a mounted position with the snap lock in the snap-in state.

In a specific aspect of the invention a medical assembly comprising a drug delivery device and a logging module is provided. The logging module is adapted to create a log of expelled dose amounts of drug from the drug delivery device when mounted thereon from a fully un-mounted to a fully mounted position along a path. The drug delivery device comprises a drug reservoir or means for receiving a drug reservoir, dose setting means, and drug expelling means for expelling a set dose. The logging module comprises electronic circuitry comprising sensor means adapted to capture a property value related to a dose amount of drug expelled from a reservoir by the expelling means during an expelling event, processor means adapted to determine dose amounts based on captured property values, and a switch operatable between an off- and an on-state when the logging module is mounted on the drug delivery device, the switch being in the on-state when the logging module is mounted within a first distance from the fully mounted position, and in the off-state when the logging module is mounted outside the first distance from the fully mounted position. The assembly further comprises a snap lock comprising co-operating mating structures arranged on the logging module respectively the drug delivery device, the snap lock being operatable from an initial state through an expanded state to a snap-in state when the logging module is mounted on the drug delivery device, the snap lock being in the snap-in state when the logging module is mounted within a second distance from the fully mounted position. The second distance is shorter than the first distance to ensure that the switch will be in the on-state before the snap lock is in the snap-in state, the electronic circuitry with the switch in the on-state being adapted to detect an error condition corresponding to a state in which the logging module is not in a mounted position with the snap lock in the snap-in state.

The drug expelling means may comprise a magnet having an initial axial position corresponding to a dose setting state, the electronic circuitry being adapted to detect the error condition based on a detected axial position of the magnet. The detected axial position need not to be an absolute position but may be a check against an expected nominal value or position relative to the module. The magnet may be configured to rotate during operation of the expelling means, the amount of rotation corresponding to the amount of drug expelled from a reservoir by the expelling means, and the electronic circuitry may be configured to determine an expelled dose amount based on determined rotational positions of the magnet.

The snap-in state may correspond to the logging module being mounted on the drug delivery device in the fully mounted position. In the fully mounted position the snap lock may be non-expanded corresponding to the initial state or it may be partially expanded. Typically, the switch will be in the on-state when the snap lock is in the expanded state, and the switch will be in the off-state when the snap lock is in the initial state.

The snap lock may be designed to have an intended small axial play when in the snap-in state, this resulting in the second distance having a positive value. Correspondingly, if no axial play is intended then the second distance is ideally zero.

The snap lock may comprise on or more flexible structures arranged on the logging module and corresponding mating non-flexible structures arranged on the drug delivery device. Alternatively the flexible structures may be arranged on the drug delivery device or on both.

In an exemplary embodiment the first logging module comprises at least one individual snap lock adapted to engage a lateral protrusion on the drug delivery device, the individual snap lock comprising a flexible wire portion adapted to be moved laterally by the lateral protrusion and subsequently snap inwardly corresponding to the snap-in state.

The drug delivery device may comprise a generally cylindrical mounting portion, and the logging module may comprise a generally cylindrical bore adapted to receive the cylindrical mounting portion. The logging module snap lock structures may be arranged corresponding to the logging module cylindrical bore.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin, however, the described module could also be used to create logs for other types of drug, e.g. growth hormone.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Figure 1A:
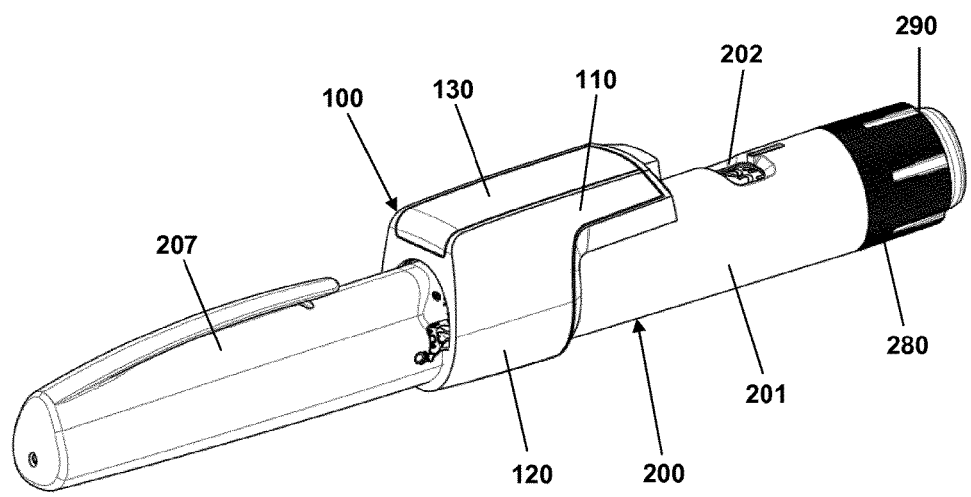
FIGS. 1A and 1B show a pen-formed drug delivery device with an electronic logging module.
Figure 1B:
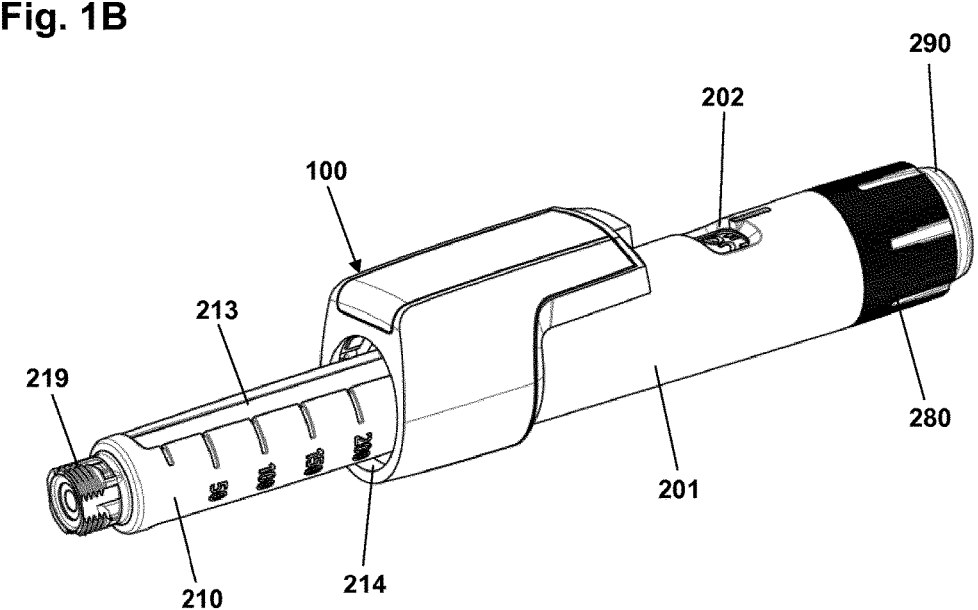

FIGS. 1A and 1B show a pen-formed drug delivery device 200 on which an electronic logging device (in the following termed logging module) 100 is mounted. In the present context the device represents a "generic" drug delivery device providing a specific example of a device in combination with which embodiments of the present invention is intended to be used or which can form a basis for aspects of the present invention.

More specifically, the logging module 100 comprises a body portion 110 and a ring-formed portion 120 allowing the module to be mounted on a generally cylindrical pen device. The body portion comprises electronic circuitry and sensor means allowing a property to be detected representing an amount of drug being expelled from the cartridge, as well as a display 130 for displaying data to a user. The ring portion comprises coupling means allowing the module to be securely and correctly mounted on the pen body. The electronic circuitry and the sensor means may in part be arranged in the ring portion.

The pen device 200 comprises a cap part 207 and a main part having a proximal body or drive assembly portion with a housing 201 in which a drug expelling mechanism is arranged or integrated, and a distal cartridge holder portion in which a drug-filled transparent cartridge 213 with a distal needle-penetrable septum is arranged and retained in place by a non-removable cartridge holder attached to the proximal portion, the cartridge holder having openings allowing a portion of the cartridge to be inspected as well as distal coupling means 219 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose member 280 serves to manually set (or dial) a desired dose of drug shown in display window 202 and which can then be expelled when the button 290 is actuated. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose.

FIGS. 1A and 1B show a drug delivery device of the pre-filled type, i.e. it is supplied with a pre-mounted cartridge and is to be discarded when the cartridge has been emptied. In alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removably attached to the main part of the device.

Figure 2:
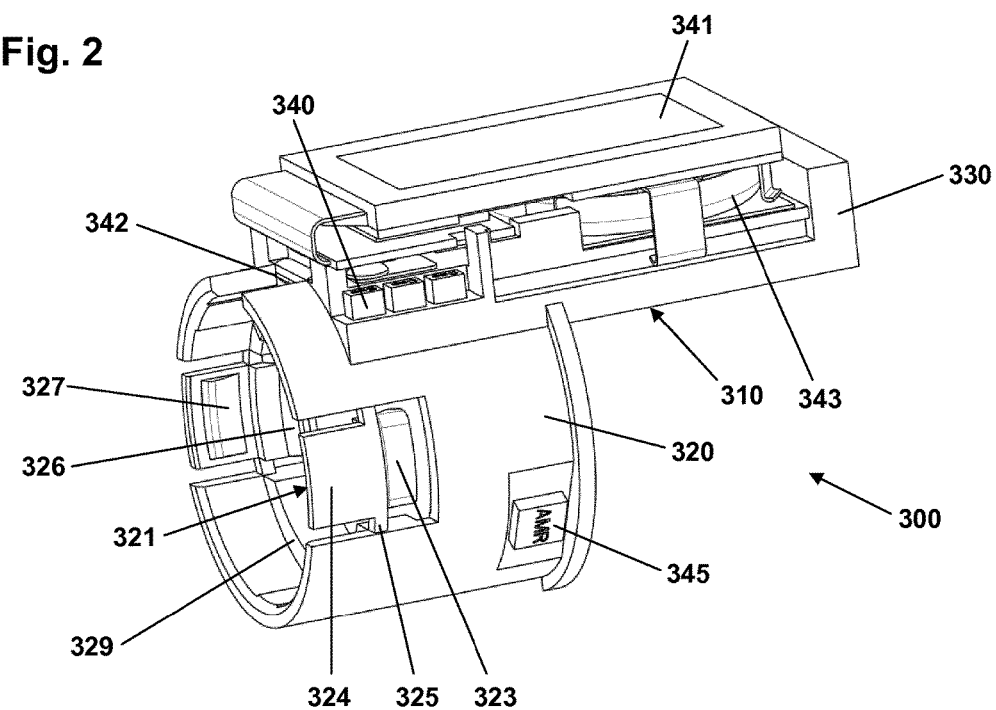
FIG. 2 shows the interior of a logging module.

Turning to FIG. 2 a first exemplary embodiment of a logging module 300 is shown in which the exterior cover portion has been removed to reveal the interior design and components, the cover portion providing the exterior oriented towards the user whereas the exterior surface facing the pen when the module is in its mounted position is made up by the main body, see below.

The module comprises a main body 310 having a generally cylindrical ring-formed portion 320 and a body portion 330 on which the majority of the electronic circuitry is mounted. The main body is formed from an LDS polymer whereby integrated wiring can be achieved by using LDS (Laser Direct Structuring) technology, the polymer having elastic properties allowing a flexible hinged latch to be formed integrally. More specifically, the ring portion comprises an inner generally cylindrical surface adapted to be mounted on a drug delivery pen body as well as a pair of opposed integrally formed coupling structures 321 adapted to engage corresponding coupling structures on the pen device to assure that the module is securely mounted. The distal part of the ring portion has a larger diameter than a distally facing circumferential stop surface 329 adapted to receive and engage a cap when the module is mounted on a pen as can be seen in FIG. 1B.

The inner ring surface and the outer pen body surface may be in either form-fitting or slight frictional engagement. Each coupling structure on the module is in the form of a latch 321 having a proximal portion 323, a distal portion 324 and a central portion, the latter being pivotally connected to the ring portion by integrally formed flexible hinges 325 allowing the latch to pivot a few degrees corresponding to a circumferential axis. By this arrangement the distal latch portion moves inwards when the proximal portion is moved outwards and vice versa. The proximal latch portions each comprises an inner protrusion 326 adapted to engage a corresponding coupling structure on the pen device and the distal latch portions each comprises a protrusion 327 adapted to engage the cap when a cap is mounted by insertion into the circumferential gap 214 (see FIG. 1B) between the logging module and the cartridge holder. To assure correct rotational mounting of the module on the pen the module is provided with a slot 518 (see FIG. 4A) adapted to axially engage a corresponding protrusion 218 (see FIG. 4A) on the pen. In the shown embodiment of FIG. 1B the protrusion is provided on the pen cartridge holder 210 and arranged opposite the pen display window 202, the electronic display 130 thereby being arranged next to the pen display window when the module is mounted on a pen. Alternatively, the electronic display may be arranged opposite the pen display window, or the design may allow a user to choose between the two rotational positions. On the body portion 330 the majority of the electronic components 340, a display 341, a cap switch 342 and a battery 343 are mounted. In the shown embodiment the logging module comprises three circumferentially arranged sensors in the form of magnetometers 345 mounted directly on the ring portion 320, the sensors as well as the majority of the electronic components being connected using LDS. The magnetometers and the electronic circuitry are adapted to detect and capture a property value related to the dose amount of drug expelled in the form of rotational movement of a magnetic member of the enclosed expelling mechanism, this as described in greater detail in WO 2014/161952 and EP 14194548.5 which are hereby incorporated by reference.

Further sensors may be provided allowing e.g. the type of the device to be recognized. For example, a sensor may be provided adapted to detect the colour of the part of the pen on which the logging module is attached or to read a correspondingly arranged barcode.

The logging module may be provided with user input means in the form of e.g. one or more buttons (not shown) allowing the user to control the module, e.g. allowing the user to browse through log entries. The logging module may further be provided with transmission means allowing data to be transmitted to or from the module, e.g. log data may be transmitted to a user's smartphone by NFC or other wireless means.

Figure 3A:
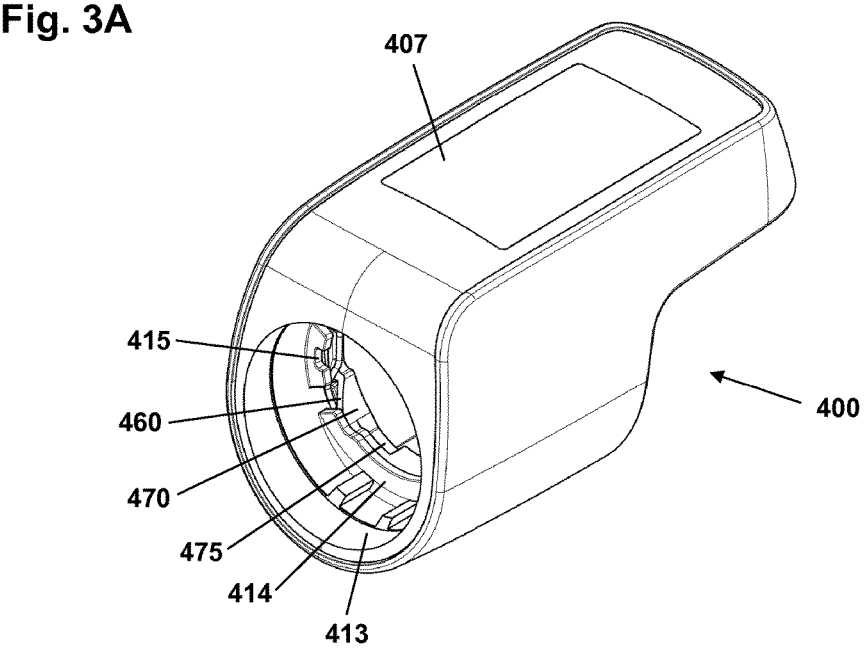
FIG. 3A shows the exterior of a further logging module.
Figure 3B:
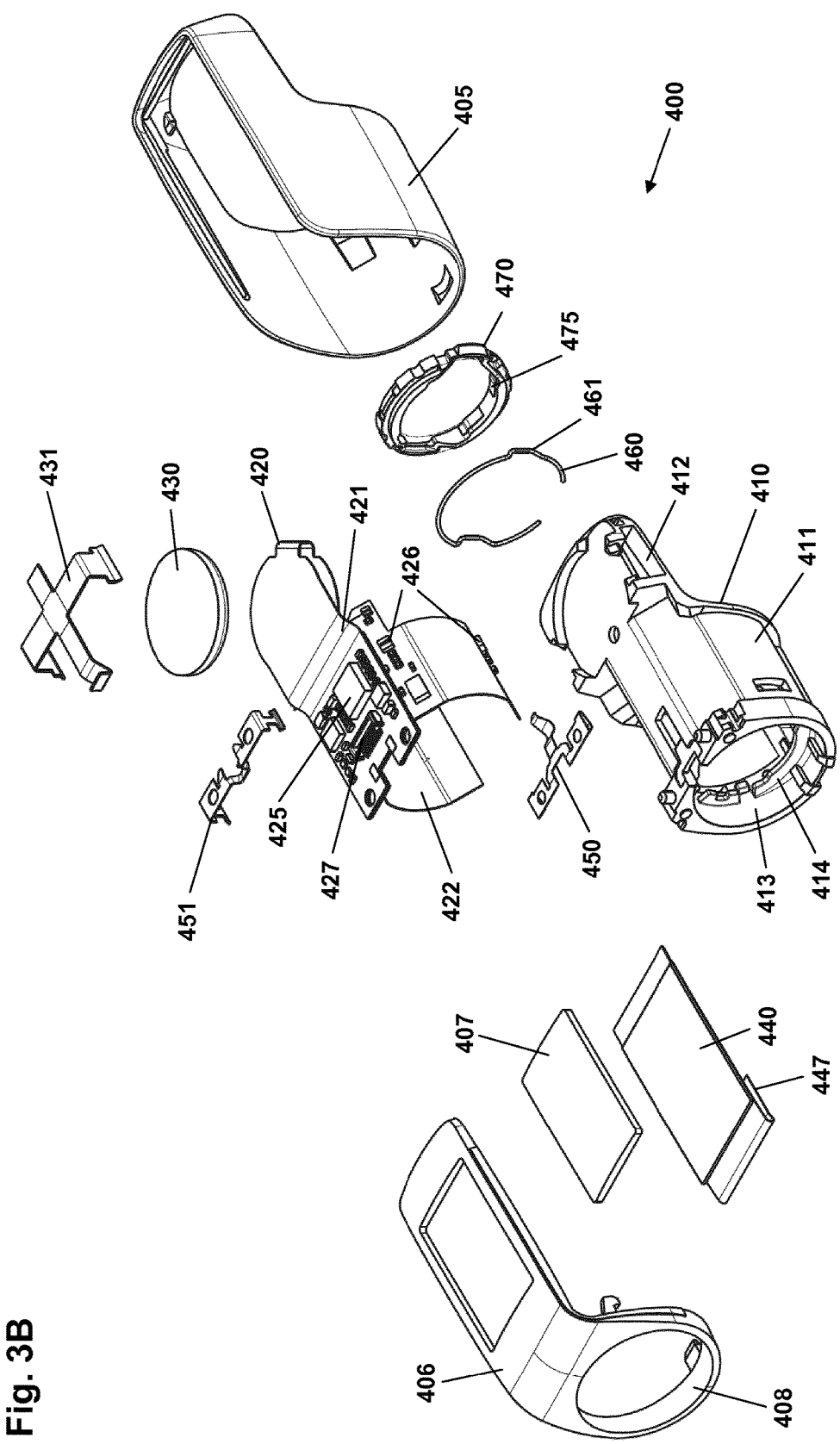
FIG. 3B shows an exploded view of the logging module of FIG. 3A, FIGS. 4A and 4B show the working principle of a snap ring coupling.

Turning to FIGS. 3A and 3B a second exemplary embodiment of a logging module 400 is shown in an assembled respectively an exploded view. The module 400 has the same general appearance as the above described logging module 100 of FIG. 1A and comprises a display window 407 and a bore 413 allowing it to be mounted on a pen device. Instead of being provided with coupling means in the form of latches 322, a flexible snap ring 460 is arranged in the bore and held in place between on the distal side a number of circumferential flange portions 414 formed as part of the housing and on the proximal side an inserted code ring 470 comprising code structures, e.g. cut-outs 475, adapted to engage corresponding code structures formed on the cartridge holder of a corresponding pen device (see below). The flange portions are provided with a pair of opposed cut-outs 415 allowing coupling protrusions on a pen cartridge holder to engage the snap ring.

Turning to the exploded view of FIG. 3B the module 400 comprises a body member 410 serving as a mounting platform for the different components of the module, the main body providing the "inner" exterior surfaces facing the pen when the module is in its mounted position, the "outer" exterior surface being provided by a cover portion 405 and a display window portion 406, the latter comprising an opening for receiving a transparent window 407 as well as a ring portion 408 forming the cap-facing surface of the module.

The body member 410 has a generally cylindrical ring-formed portion 411 providing a bore 413, and an "upper" portion with an extension 412 on which the majority of the electronic circuitry is mounted. A number of double-sided adhesive tape strips (not shown) are attached to the body member serving to securely hold the flexible printed circuit board (PCB) 420 in place, the PCB comprising a main portion 421 and a pair of opposed "wing" portions 422 adapted to be mounted on the ring-portion. On the PCB a number of electronic components 425, a number of magnetometers 426 as well as a display contact 427 are mounted. The wing portions mainly serve to circumferentially arrange the magnetometers on the ring-portion. A button power cell 430 is connected to the PCB and held in place by a clip 431 adapted to engage the body member. A display 440 is adapted to be mounted on top on the main PCB portion via a flex ribbon cable 447. A body switch member 450 is adapted to be mounted on the body member and cooperate with the PCB, the switch detecting when the logging module has been mounted on a pen body. A cap switch member 451 is adapted to be mounted on the body member and cooperate with the PCB, the switch detecting when the pen cap 207 (see FIG. 1A) is mounted on the pen.

A wire snap member 460 in the form of an open ring is adapted to be mounted in the distally-facing opening of the body member bore. The snap member comprises a pair of opposed coupling sections 461 and serves to reversibly lock the module in place when mounted on a pen body. The wire snap member is described in greater detail below. A code ring 470 is adapted to be mounted in the bore proximally of the snap member and cooperate with a corresponding coding structure on the pen device, i.e. by means of a key-and-slot coding. The coding serves to ensure that a given module can be mounted only on the type of pen device to which it is adapted to work, e.g. comprising a given drug in a given concentration. The code ring may also serve to provide a colour coding corresponding to the given coding, this allowing the module to be formed generally in a "generic" colour. The code ring may be used to hold the snap ring in place in the bore. In alternative embodiments the code structures may be arranged on other parts of the logging module and pen.

Figure 4A:
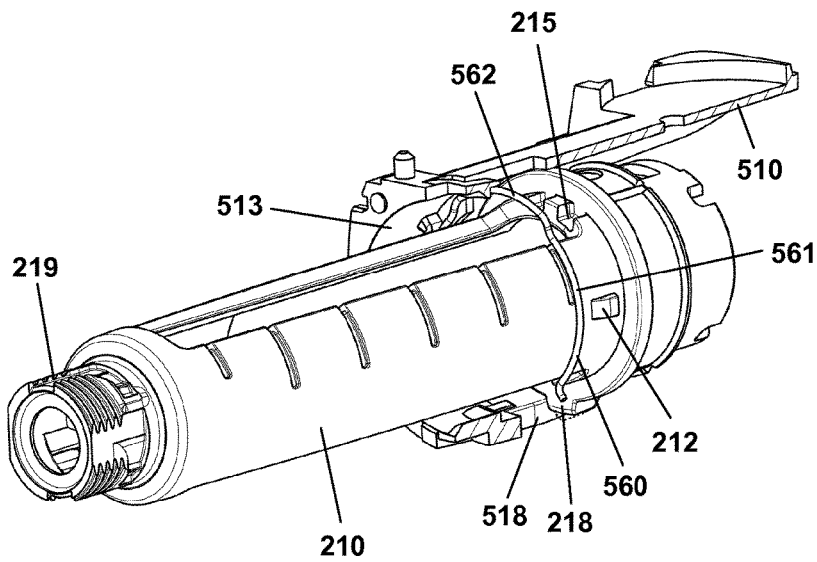
Figure 4B:
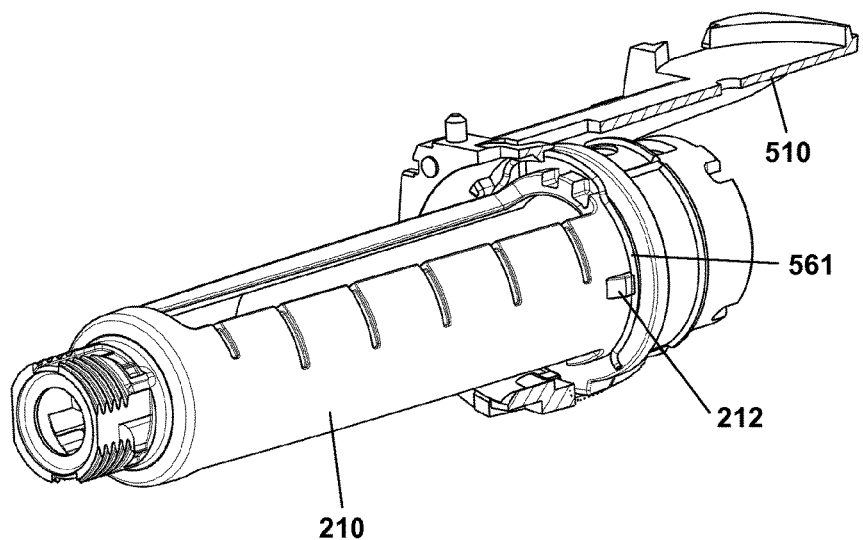

Turning to FIGS. 4A and 4B an alternative embodiment of a module body member 510 with a bore 513 is shown in cross-section, the body member being provided with an open wire snap ring member 560 having a central portion 562 adapted to engage the body member as well as two opposed leg portions 561 each adapted to provide an individual reversible snap lock when engaging corresponding snap coupling means on e.g. a pen cartridge holder. In the shown embodiment the pen snap coupling means is in the form of a pair of opposed snap protrusions 212 provided proximally on a pen cartridge holder 210, the protrusions also serving to lock a pen cap in place when no logging module is mounted on the pen. In the shown embodiment the cartridge holder proximal portion is provided with a code structure in the form of a pair of cut-outs 215, the code structure being adapted to engage corresponding code protrusions formed on e.g. a code ring (not shown). The module body member 510 comprises a slot 518 adapted to axially engage cartridge holder protrusion 218 to thereby rotationally position the module on the pen body.

In FIG. 4A the logging module has been partly mounted on a pen (only the cartridge holder is shown), the snap ring abutting the distally-facing sloped surface of the coupling protrusions. When the logging module is moved to its fully mounted position each snap ring leg portion expands laterally and then snaps in place proximally of the coupling protrusion. As the proximally-facing slopes of the coupling protrusions are steeper than the distally-facing slopes the force required to remove the logging device from the pen is greater than when mounting it. The shown snap ring has an open configuration, however, alternatively it may be in the form of a closed ring as long the snap portions of the ring are allowed to move as required by the functionality. As a further alternative the snap ring may be replaced with individual pieces of wire, e.g. for each individual snap coupling, such a wire piece being straight or curved.

Figure 5A:
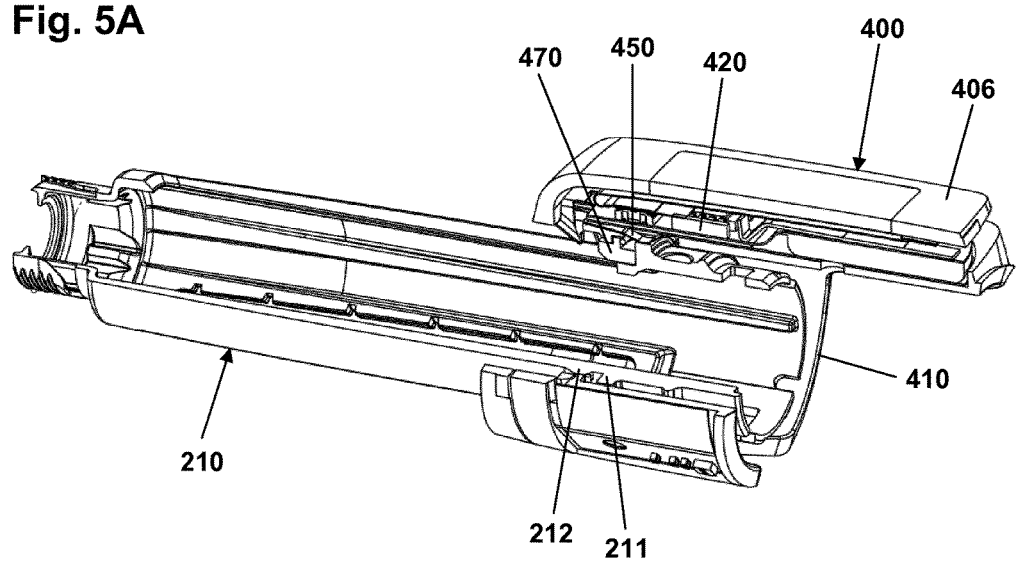
FIG. 5A shows in a sectional view the logging module of FIG. 3B mounted on a cartridge corresponding to a first state.
Figure 5B:
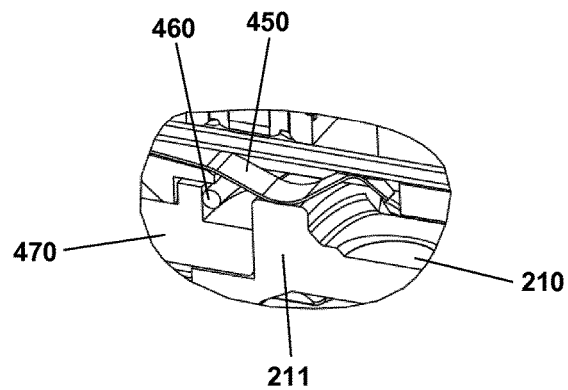
FIG. 5B shows in detail the switch of FIG. 5A.

FIG. 5A shows in a sectional view the logging module 400 of FIG. 3B mounted on a cartridge holder 210 corresponding to the cartridge holder shown in FIGS. 1B and 4A. As described with reference to FIG. 3B the module comprises a body member 410, a display window portion 406, a code ring 470, a snap ring 460 (see FIGS. 5B and 5C), electronic circuitry arranged on a flexible PCB 420, and body switch member 450. The cartridge holder 210 comprises a circumferential flange 211 and a pair of opposed snap protrusions 212. FIG. 5B shows the body switch member 450 in detail and FIG. 5C shows the cartridge holder snap protrusions 212 and snap ring 460 in detail.

Figure 5C:
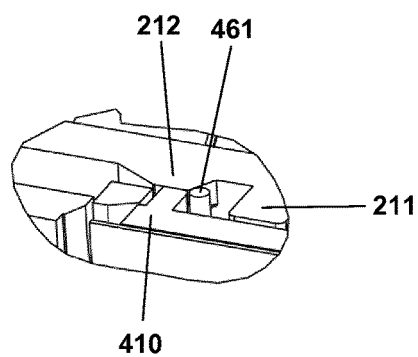
FIG. 5C shows in detail the snap lock of FIG. 5A.

FIGS. 5A-5C show the logging module in its fully mounted state in which the snap ring coupling sections 461 have snapped in place behind the cartridge holder snap protrusions 212, and the body switch member 450 has been deflected by the cartridge holder flange 211 into contact with the corresponding contact point on the PCB to thereby turn on the switch and indicate to the electronics that the module has been mounted on a pen device. As appears from FIG. 5C, in this embodiment the snap ring does not fully seat behind the snap protrusions but is "parked" slightly expanded on the proximally-facing slope of the protrusion.

Figure 6A:
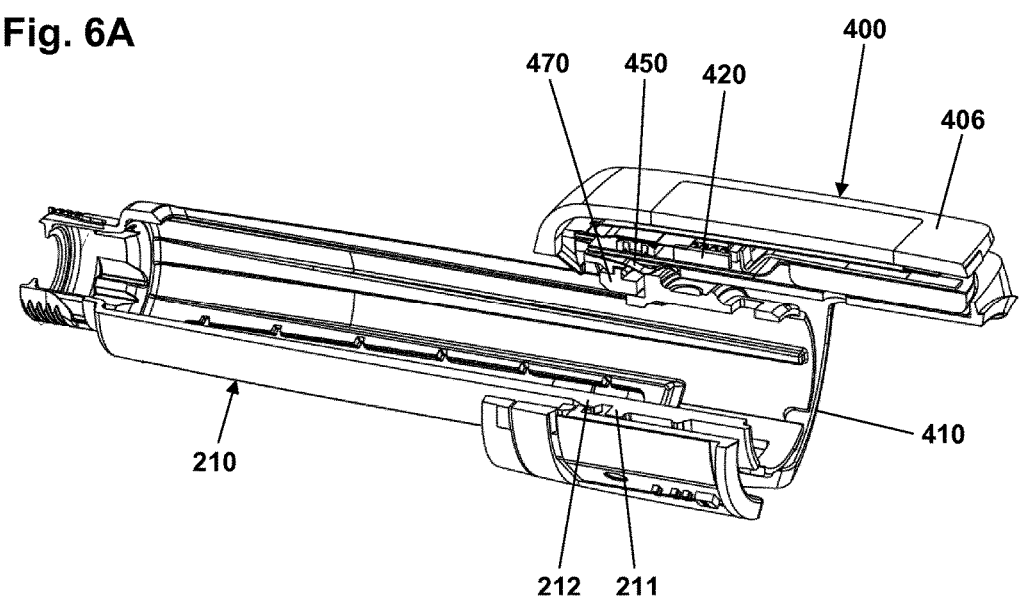
FIG. 6A shows in a sectional view the logging module of FIG. 3B corresponding to a second state.
Figure 6B:
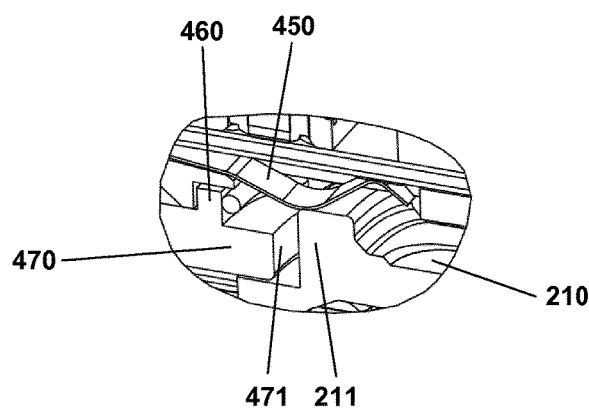
FIG. 6B shows in detail the switch of FIG. 6A.
Figure 6C:
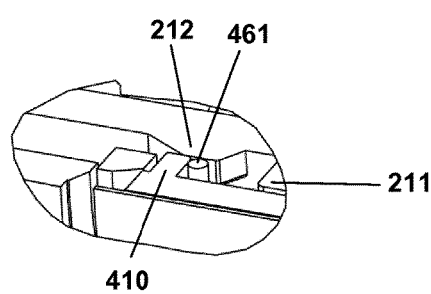
FIG. 6C shows in detail the snap lock of FIG. 6A.

FIGS. 6A-6C correspond to FIGS. 5A-5C and show the state in which the logging module has been partly mounted with the expanded snap ring coupling sections 461 "parked" on top of the cartridge holder snap protrusions 212. Correspondingly, until the snap ring fully snaps into its locked position behind the snap protrusion (or on the slope as shown in FIG. 5C) the module will be in a non-fully mounted position. The situation may arise if e.g. a small piece of material has been trapped in a gap 471 between the module and the pen, see FIG. 6B.

Aspects of the present invention address this kind of situation in which the module is not fully mounted on the pen as described above, and in which the user is not aware of this. Indeed, if the module snap ring has not engaged the locking protrusion at all, the module will be loosely arranged on the pen and tend to fall off which situation can be assumed to be readily recognisable by the user. As the working principle of the above-described logging module is based on detection of relatively weak magnetic fields originating from a moving magnetic member inside the pen, it is important that the two units are arranged correctly in their specified position relative to each other to ensure proper and correct detection of dose amounts. Correspondingly, if the logging module is not fully and correctly mounted detected values may be incorrect or no values may be detected at all.

Addressing the partly-mounted situation, the logging module 400 is designed to perform a position test when it has been mounted on the pen and communicate to the user if the position is not correct, i.e. the module is not in its fully mounted position with the magnetometers thereby in the correct position relative to the magnetic member. To ensure that the test is performed the body switch member 450 is arranged in such a way relative to the snap ring that it is activated before the snap ring snaps in place, this allowing the position test to be performed with the snap ring still in its fully or partly expanded state. Indeed, both the switch and the snap ring are designed for cooperation with a given cartridge holder having the flange and the snap protrusions arranged at specified positions.

By the above arrangement three general mounting scenarios are addressed: (i) The snap ring does not engage the cartridge holder snap protrusions at all and the body switch is not activated. No position test is performed, however, as the module is only very loosely arranged on the pen, it can be assumed that it will be apparent to the user that the module is not correctly mounted and therefore that no dose amount will be detected and logged. (ii) The snap ring engages the snap protrusions but does not fully snap in place, however, the body switch has at this point been activated, this allowing a position test to be performed. If the position test results in the detection of a not-correctly-mounted position the user is informed, e.g. by information in the display and/or by an audible alarm, this informing the user that the mounting has to be checked. (iii) The snap ring fully snaps in place behind the cartridge holder protrusions and the body switch is activated, this allowing a position test to be performed.

The position test could be a position test per se or it could be a functional test. In the first case the logging module may be provided with detecting means allowing the position of a given structure to be checked by e.g. mechanical or optical means. For example, optical means may be used to check whether a given structure is located within a predetermined positional range. For a pen device of the above-described type, such a structure could be the transition between the cartridge holder and the pen body, the two structures having e.g. different colours. Alternatively specific indicia may be located on the pen, e.g. a given surface marking the position of which can then be identified.

Alternatively, the logging device may be provided with detection means allowing a functional test to be performed. For example, in the above-described example the logging device is provided with magnetometers and electronic circuitry adapted to detect and capture the position of a magnetic member enclosed in the pen expelling mechanism before, during and after a dose of drug has been expelled. As disclosed in WO 2014/161952 and EP 14194548.5 for an expelling mechanism in which the magnetic member in addition to being rotated during dose expelling is also moved axially during an expelling event, also the axial position of the magnetic member can be detected.

Correspondingly, the ability to detect the axial position of an interior element in the pen device, e.g. a magnetic member, can be used to check that the logging device is correctly mounted axially on the pen device, the magnetic member having a well-defined axial position, i.e. the dose setting position.

Figure 7:
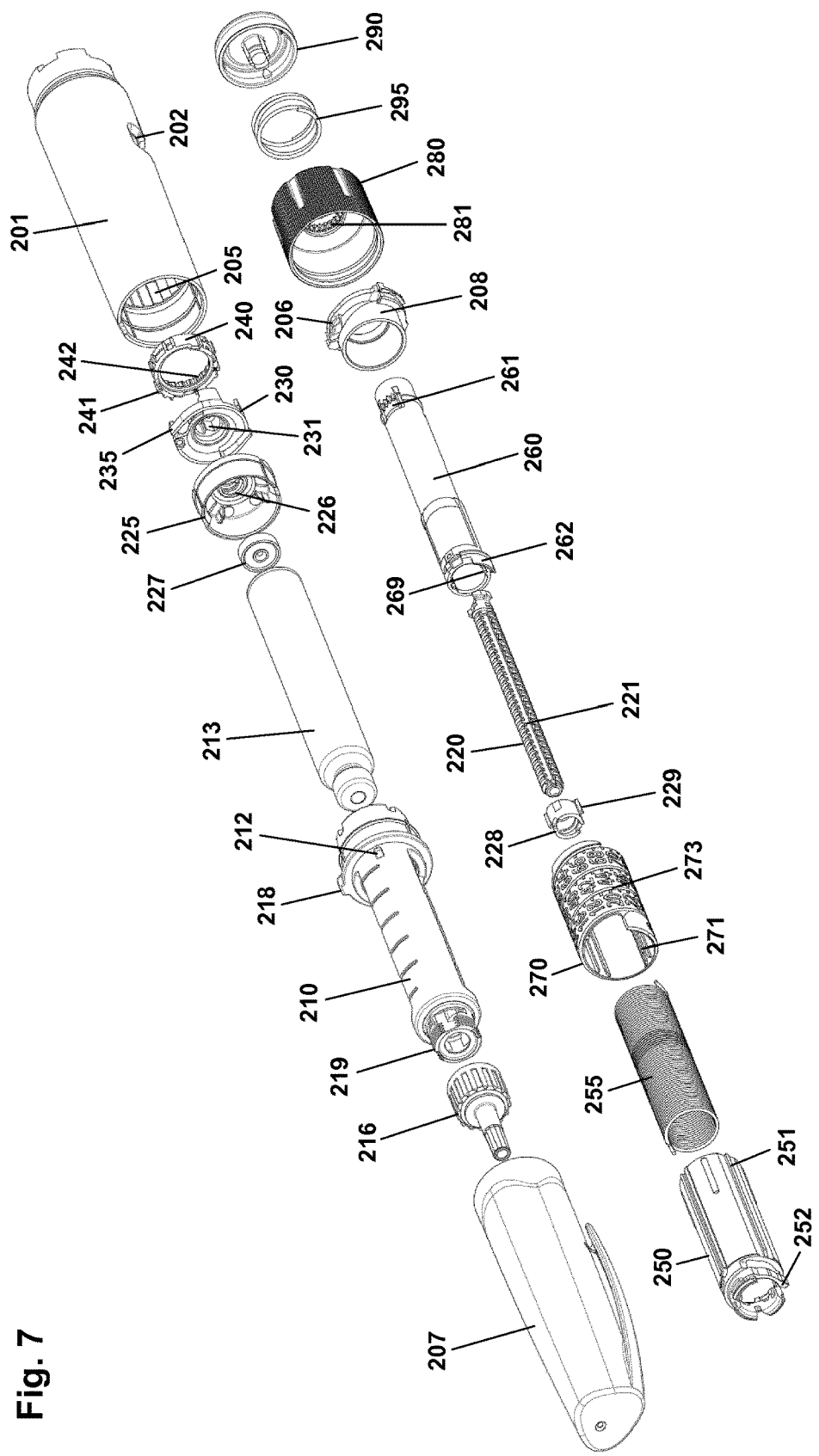
FIG. 7 shows an exploded view of a pen-formed drug delivery device.

An example of a drug delivery device comprising a magnetic member allowing such error detection will be described with reference to FIG. 7 showing an exploded view of the pen-formed drug delivery device 200 shown in FIG. 1A.

More specifically, the pen comprises a tubular housing 201 with a window opening 202 and onto which a cartridge holder 210 is fixedly mounted, a drug-filled cartridge 213 being arranged in the cartridge holder. The cartridge holder is provided with distal coupling means 219 allowing a needle assembly 216 to be releasably mounted, proximal coupling means in the form of two opposed snap protrusions 212 allowing a cap 207 to be releasably mounted covering the cartridge holder and a mounted needle assembly, as well as a protrusion 218 preventing the pen from rolling on e.g. a table top. In the housing distal end a nut element 225 is fixedly mounted, the nut element comprising a central threaded bore 226, and in the housing proximal end a spring base member 208 with a central opening is fixedly mounted. A drive system comprises a threaded piston rod 220 having two opposed longitudinal grooves and being received in the nut element threaded bore, a ring-formed piston rod drive element 230 rotationally arranged in the housing, and a ring-formed clutch element 240 which is in rotational engagement with the drive element, the engagement allowing axial movement of the clutch element. The clutch element is provided with outer spline elements 241 adapted to engage corresponding splines on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 231 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 235 adapted to engage corresponding ratchet teeth 205 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system to the drive system.

On the piston rod an end-of-content (EOC) member 228 is threadedly mounted and on the distal end a washer 227 is rotationally mounted. The EOC member comprises a pair of opposed radial projections 229 for engagement with the reset tube.

The dial system comprises a ratchet tube 250, a reset tube 260, a scale drum 270 with an outer helically arranged row of dose numerals, a user-operated dial member 280 for setting a dose of drug to be expelled, a release button 290 and a torque spring 255. The reset tube is mounted axially locked inside the ratchet tube but is allowed to rotate a few degrees. The reset tube comprises on its inner surface two opposed longitudinal grooves 269 adapted to engage the radial projections 229 of the EOC member, whereby the EOC can be rotated by the reset tube but is allowed to move axially. The clutch element is mounted axially locked on the outer distal end portion of the ratchet tube 250, this providing that the ratchet tube can be moved axially in and out of rotational engagement with the housing via the clutch element. The dial member 280 is mounted axially locked but rotationally free on the housing proximal end, the dial ring being under normal operation rotationally locked to the reset tube, whereby rotation of dial ring results in a corresponding rotation of the reset tube and thereby the ratchet tube. The release button 290 is axially locked to the reset tube but is free to rotate. A return spring 295 provides a proximally directed force on the button and the thereto mounted reset tube. The scale drum 270 is arranged in the circumferential space between the ratchet tube and the housing, the drum being rotationally locked to the ratchet tube via co-operating longitudinal splines 251, 271 and being in rotational threaded engagement with the inner surface of the housing via cooperating thread structures, whereby the row of numerals passes the window opening 202 in the housing when the drum is rotated relative to the housing by the ratchet tube. The torque spring is arranged in the circumferential space between the ratchet tube and the reset tube and is at its proximal end secured to the spring base member 208 and at its distal end to the ratchet tube, whereby the spring is strained when the ratchet tube is rotated relative to the housing by rotation of the dial member. A ratchet mechanism with a flexible ratchet arm 252 is provided between the ratchet tube and the clutch element, the latter being provided with an inner circumferential teeth structure 242, each tooth providing a ratchet stop such that the ratchet tube is held in the position to which it is rotated by a user via the reset tube when a dose is set. In order to allow a set dose to be reduced a ratchet release mechanism 262 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

A detailed description of the operation of the mechanism of FIG. 7 can be found in WO 2014/161952 and EP 14194548.5.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. An assembly comprising a drug delivery device and a logging module adapted to create a log of expelled dose amounts of drug, the logging module being adapted to be mounted on the drug delivery device from a fully unmounted to a fully mounted position along a path, the drug delivery device comprising:
   a drug reservoir or structure for receiving a drug reservoir,
   dose setting structure, and
   drug expelling structure for expelling a set dose,
the logging module comprising electronic circuitry comprising:
   sensor structure adapted to capture a property value related to a dose amount of drug expelled from a reservoir by the expelling structure during an expelling event,
   processor structure adapted to determine dose amounts based on captured property values,
   a switch operatable between an off- and an on-state when the logging module is mounted on the drug delivery device, the switch being in the on-state when the logging module is mounted within a first distance from the fully mounted position, and in the off-state when the logging module is mounted outside the first distance from the fully mounted position, and
the assembly comprising:
   a snap lock comprising co-operating mating structures arranged on the logging module respectively the drug delivery device, the snap lock being operatable from an initial state through an expanded state to a snap-in state when the logging module is mounted on the drug delivery device, the snap lock being in the snap-in state when the logging module is mounted within a second distance from the fully mounted position,
wherein:
   the second distance is shorter than the first distance to ensure that the switch will be in the on-state before the snap lock is in the snap-in state, and
   the electronic circuitry with the switch in the on-state is adapted to detect an error condition corresponding to a state in which the logging module is not in a mounted position with the snap lock in the snap-in state.

2. An assembly as in claim 1, wherein the drug expelling structure comprises a magnet (240) having an initial axial position corresponding to a dose setting state, the electronic circuitry being adapted to detect the error condition based on a detected axial position of the magnet.

3. An assembly as in claim 2, wherein:
   the magnet is configured to rotate during operation of the expelling structure, the amount of rotation corresponding to the amount of drug expelled from a reservoir by the expelling structure, and
   the electronic circuitry is configured to determine an expelled dose amount based on determined rotational positions of the magnet.

4. An assembly as in claim 1, wherein the snap-in state corresponds to the logging module being mounted on the drug delivery device in the fully mounted position.

5. An assembly as in claim 1, wherein the switch is in the on-state when the snap lock is in the expanded state.

6. An assembly as in claim 1, wherein the switch is in the off-state when the snap lock is in the initial state.

7. An assembly as in claim 1, wherein the snap lock comprises a flexible structure arranged on the logging module and a mating non-flexible structure arranged on the drug delivery device.

8. An assembly as in claim 7, wherein the logging module comprises at least one individual snap lock member adapted to engage a lateral protrusion on the drug delivery device, the individual snap lock member comprising a flexible wire portion adapted to be moved laterally by the lateral protrusion and subsequently snap inwardly corresponding to the snap-in state.

9. An assembly as in claim 1, wherein the snap lock comprises a flexible structure arranged on the drug delivery device and a mating non-flexible structure arranged on the logging module.

10. An assembly as in claim 1, wherein:
 the drug delivery device comprises a generally cylindrical mounting portion, and
 the logging module comprises a generally cylindrical bore adapted to receive the cylindrical mounting portion.

11. An assembly as in claim 10, wherein the logging module snap lock structure(s) is/are arranged corresponding to the logging module cylindrical bore.

* * * * *